United States Patent [19]
Grendahl

[11] Patent Number: 4,919,663
[45] Date of Patent: * Apr. 24, 1990

[54] LAMINATED ZONE OF FOCUS ARTIFICIAL HYDROGEL LENS

[76] Inventor: Dennis T. Grendahl, 2070 Shoreline Dr., Orono, Minn. 55391

[*] Notice: The portion of the term of this patent subsequent to Jan. 17, 2006 has been disclaimed.

[21] Appl. No.: 258,028

[22] Filed: Oct. 17, 1988

Related U.S. Application Data

[63] Continuation-in-part of Ser. No. 88,428, Aug. 24, 1987, Pat. No. 4,798,609.

[51] Int. Cl.$^5$ .............................................. A61F 2/16
[52] U.S. Cl. ..................................................... 623/6
[58] Field of Search ...................... 623/654, 6; 351/168

[56] References Cited

U.S. PATENT DOCUMENTS

| | | | |
|---|---|---|---|
| 3,877,798 | 4/1975 | Tolan | 351/168 |
| 4,240,163 | 12/1980 | Galin | 623/6 |
| 4,704,016 | 11/1987 | deCarle | 623/6 |
| 4,798,608 | 1/1989 | Guendahl | 623/6 |

FOREIGN PATENT DOCUMENTS

| | | | |
|---|---|---|---|
| 0162573 | 11/1985 | European Pat. Off. | 623/6 |
| 2181355 | 4/1987 | United Kingdom | 623/6 |

Primary Examiner—Richard J. Apley
Assistant Examiner—James Prizant
Attorney, Agent, or Firm—Hugh D. Jaeger

[57] ABSTRACT

An implantable or contact hydrogel lens for replacement of a defective natural lens in an eye in which various portions of the lens are laminated horizontally to have different powers to produce in-focus images on different portions of the retina of objects which are located at various distances from the eye, thereby substituting for the natural focusing action of the eye. The image processing capability of the brain functions to largely ignore the out-of-focus images and concentrate on the in-focus image of the object selected by the brain for consideration.

8 Claims, 8 Drawing Sheets

FIG. I

LAMINATED ZONE OF FOCUS ARTIFICIAL HYDROGEL LENS

CROSS REFERENCE TO CO-PENDING APPLICATIONS

This Application is a Continuation-in-Part of Application Ser. No. 07/088,428, filed Aug. 24, 1987, entitled "Laminated Zone of Focus Artificial Lens", now U.S. Pat. No. 4,798,609; which is related in part to Application Ser. No. 07/258,019, filed Oct. 17, 1988, entitled "Multiple Element Zone of Focus Artificial Hydrogel Lens", which is a Continuation-in-Part of Application Ser. No. 07/088,412, filed Aug. 24, 1987, entitled "Multiple Element Zone of Focus Artificial Lens", now U.S. Pat. No. 4,778,462; Application Ser. No. 07/258,027, filed Oct. 17, 1988, entitled "Cylindrically Segmented Zone of Focus Artificial Hydrogel Lens", which is a Continuation-in-Part of Application Ser. No. 07/088,413, filed Aug. 24, 1987, entitled "Cylindrically Segmented Zone of Focus Artificial Lens", now U.S. Pat. No. 4,795,462; and Application Ser. No. 07/258,029, filed Oct. 17, 1988, entitled "Radially Segmented Zone of Focus Artificial Hydrogel Lens", which is a Continuation-in-Part of Application Ser. No. 07/088,249, filed Aug. 24, 1987, entitled "Radially Segmented Zone of Focus Artificial Lens", now U.S. Pat. No. 4,798,609.

BACKGROUND OF THE INVENTION

1. Field of the Invention

The present invention pertains to an implantable intraocular lens and, more particularly, pertains to a hydrogel lens containing laminated zone of focus lens elements.

This lens relates to hydrogel lenses which have discrete areas which serve to bring impinging rays to a focus in a specific area of the focal plane. Such lenses are called zone of focus lenses and are particularly useful for implantation into the eye as a substitute for the natural lens since, in combination with the brain, they effectively replicate the ability of the natural lens to bring objects at varying distances to a sharp focus.

The invention relates specifically to a zone of focus lens in which the hydrogel lens is a laminated structure comprising a number of laminated planar or curved hydrogel elements. The incident rays are brought to a focus on a portion of the retina and are dependent on the number of lens elements traversed by the ray. The lens area common to each combination of laminated lens elements serves to bring the rays from a given object passing through the area to a focus on a predetermined region of the retina. By selecting various powers for the hydrogel lens element laminate areas, it is possible to have an object at a given distance brought to an acceptable focus by at least one of the lens element laminated areas. In this manner, an in-focus image or sharp image is created on a particular portion of the retina serviced by that area. It has been found that the processing of the image by the brain results in the selective consideration of the sharpest image and the virtual discard of the other out-of-focus images created by the areas.

2. Description of the Prior Art

Limited attempts to produce a lens having areas of varying powers have been made. There have been many attempts to produce implantable lenses which serve for both close and far seeing, similar to bifocal spectacles. In general, such lenses have been produced with two regions having different powers. The light which impinges on the retina passes through one region to the exclusion of the other. In such a system, only one region of the lens is used at a time and there is no accommodation of the brain to reject an out-of-focus image. Great care and accuracy must be used in the preoperative measurements since both the near and far powers must be accurately determined. Since the near and far powers are not specifically interrelated, the inventory requirements are compounded since a variety of near powers must be available for every far power.

Further, the rigid materials used for lenses have required relatively large incisions for implantation, but the post-operative recovery period is shorter when a small incision is made.

The present invention overcomes the disadvantages of the prior art by providing a hydrogel lens which includes two or more laminated lens elements where each hydrogel lens element is of a different power.

SUMMARY OF THE INVENTION

The lens is a composite of laminate hydrogel lens elements. The lens area common to a given combination of lens elements has a given focal length and brings the impinging rays to bear on a predetermined, unique, portion of the retina. The common areas are selected to have a sufficient range of powers to accommodate the projected use. That is, the value of the power and the number of areas will be determined by the projected use. Most uses can be accommodated with a lens having two or three powers to accommodate objects at near, far and intermediate distances. The distribution of powers among the areas need not be done equally. For example, if most of the sight is required at close distances, the area for this distance can be increased and the area for far vision correspondingly decreased.

Accommodation of the brain to such an arrangement may be enhanced by adding a distinctive color to the areas of like power. This approach may be utilized where loss or impairment of color vision is of little consequence.

Areas of differing powers can be provided by grinding or otherwise forming a uniform lens surface over a composite laminated structure of laminate hydrogel elements having differing indices of refraction.

Lens is a generic term for intraocular lens, intracorneal lens, or contact lens. Lenses also include any optical lens such as cameras, television, telescopes, projectors, optical instruments, glasses, etc.

It is a principal object hereof to provide a laminated zone of focus hydrogel lens.

It is therefore an object of this invention to provide a very low cost zone of focus hydrogel lens which will make the replacement of a defective natural lens available to many who cannot now afford the operation.

It is another object of the invention to provide a minimum cost zone of focus hydrogel lens which does not require either an extensive inventory of various powers and combination of powers or extensive preoperative measurement prior to implantation into the eye as a replacement for a defective lens.

Still another object of this invention is to provide a very low cost approach to the replacement of a defective lens by providing a very nearly universal hydrogel lens which provides vision adequate to allow a normal life style.

These lenses can be used as replacements for the presbyoptic lens of the aging population and thereby allowing for both near and distant vision without the use of spectacles. Intraocular lenses sometimes become decentered. Distant and near vision with this zone of focus lens will not be affected by decentration.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
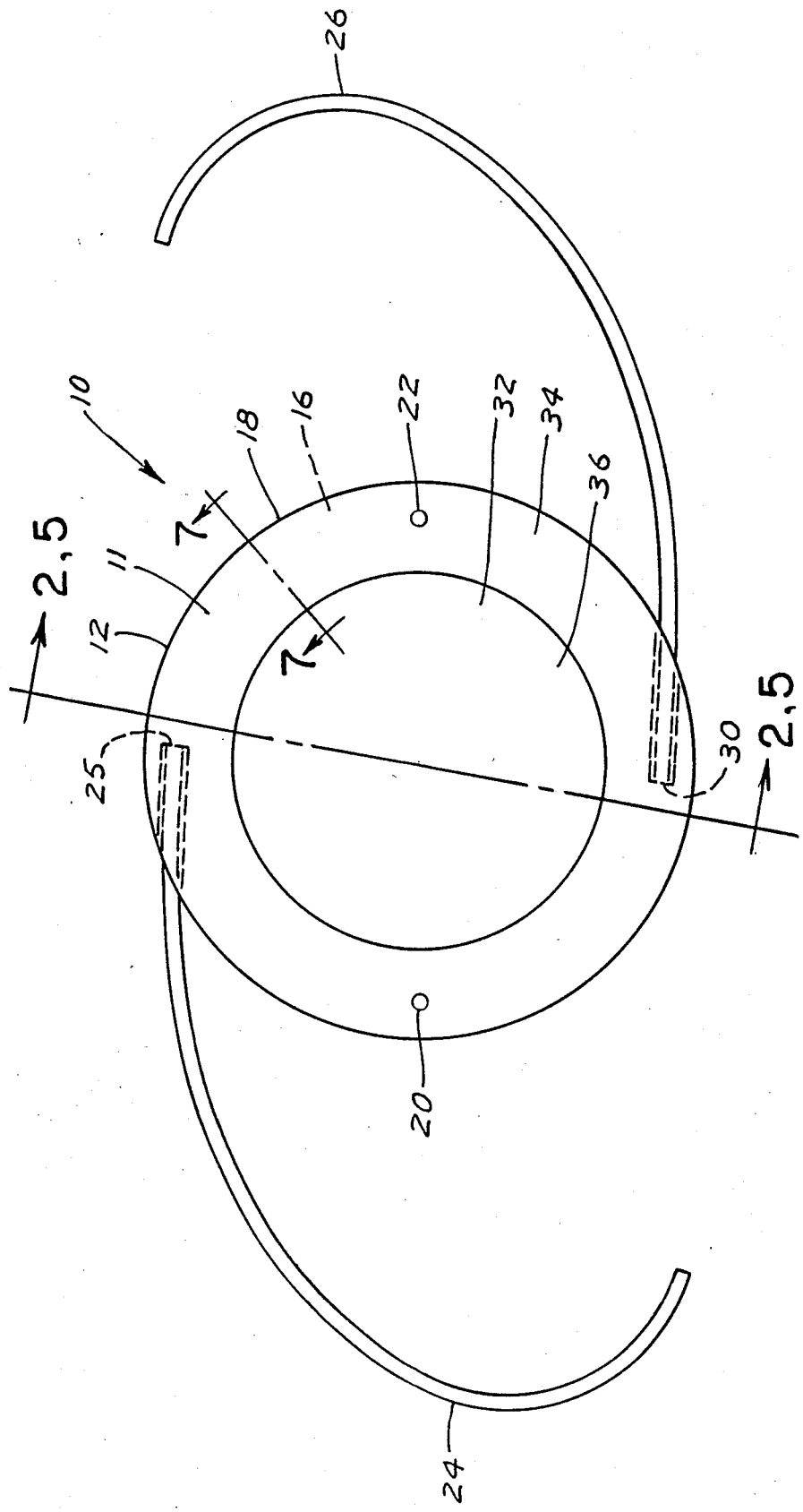
FIG. 1 illustrates a plan view of a laminated zone of focus hydrogel lens according to this invention.

FIG. 1 illustrates an implantable lens 10 of hydrogel including an optic 12, a convex anterior surface 14, a plano surface 16, an edge 18 therebetween, positioning holes 20 and 22, open loop haptics 24 and 26 engaged in holes 28 and 30 for fixation of the lens to the interior of the eye. The optic 12 includes a lens element 32 laminated to another lens element 34 of different diameters. The shape of lens 10 may be varied to accommodate optical or other requirements and is primarily illustrated as plano convex, but may be a meniscus or biconvex configuration or any other desired shape. The lens optic 12 includes a plurality of convex lens elements 32 and 34. A smooth coating 36 is applied over the lens optic 12 to form a smooth convex anterior surface 14. Each of the lens elements 32 and 34 has a distinct focal length or power so as to bring objects of differing distance into focus in a common focal plane. It will be appreciated that the incident rays passing through both lens elements 32 and 34 will be diffracted according to the sum of the powers of these two elements while those which pass only through element 34 will be diffracted according only to the power of that element. By careful choice of the respective powers of these lens elements 32 and 34, it is possible to bring exterior objects at near or far distances from the lens 10 to focus on the retina. Such an arrangement will accommodate vision at near and far distances similar to the operation of bifocal spectacles.

Fabrication of the hydrogel lens shown in FIG. 1 may be accomplished by first completing the shaping of lens element 34 in conventional fashion according to the shape desired. Lathe cutting, grinding or molding techniques may be used, although molding will generally be preferred because of the potential for lower cost when large numbers of elements are made. Subsequent to the production of lens element 34, the lens element 32 is laminated to the lens element 34. The lens element 32 may simply be a planar circular element with sufficient flexibility to allow it to conform to element 34 during the lamination process. The lens element 32 may also be a separately molded or lathe cut element having one surface which matches the abutting surface of element 34, and an additional optical characteristic, such as prismatic correction, an aspheric or spherical surface, or simply a spherical surface on the side opposite that which is laminated to element 34. Lamination can be accomplished by the use of a transparent adhesive material such as Eastman 910 or by other satisfactory bonding techniques such as ultrasonic bonding, heating or suitable solvents or sequential casting techniques.

Since the hydrogel lens 10 is a composite structure, it is possible to make a variety of powers by different combinations of elements. While the lens of FIG. 1 shows the use of two lens elements, it will be appreciated that three or even more lens elements could be used. When more lens elements are used, it becomes possible to produce a wider variety of powers simply be selecting various combinations of elements. Since fewer basic elements are used, the cost of manufacture of such lens elements is lower than would otherwise be the case. Further, the increase in numbers to be produced would allow the use of relatively inexpensive tooling for such processes as molding, which could provide a lower ultimate cost to the consumer.

Figure 2:
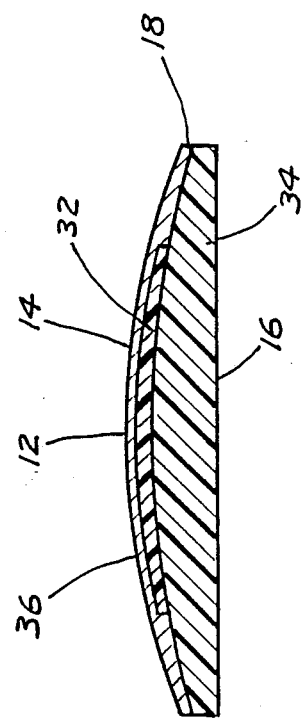
FIG. 2 illustrates a cross-sectional view taken along line 2—2 of FIG. 1.

FIG. 2 illustrates a sectional view taken along line 2—2 of FIG. where all numerals correspond to those elements previously described. The hydrogel lens elements 32 and 34 are laminated with a suitable adhesive material or solvent to form the laminated composite lens 10. The surfaces of the lens elements 32 and 34 may have any configuration, provided that the corresponding surfaces match so as to accommodate lamination. If the lens element 32 is of a thin hydrogel material, it may be possible to simply laminate the circular planar lens element 34 to the corresponding surface of the lens element 34.

Figure 3:
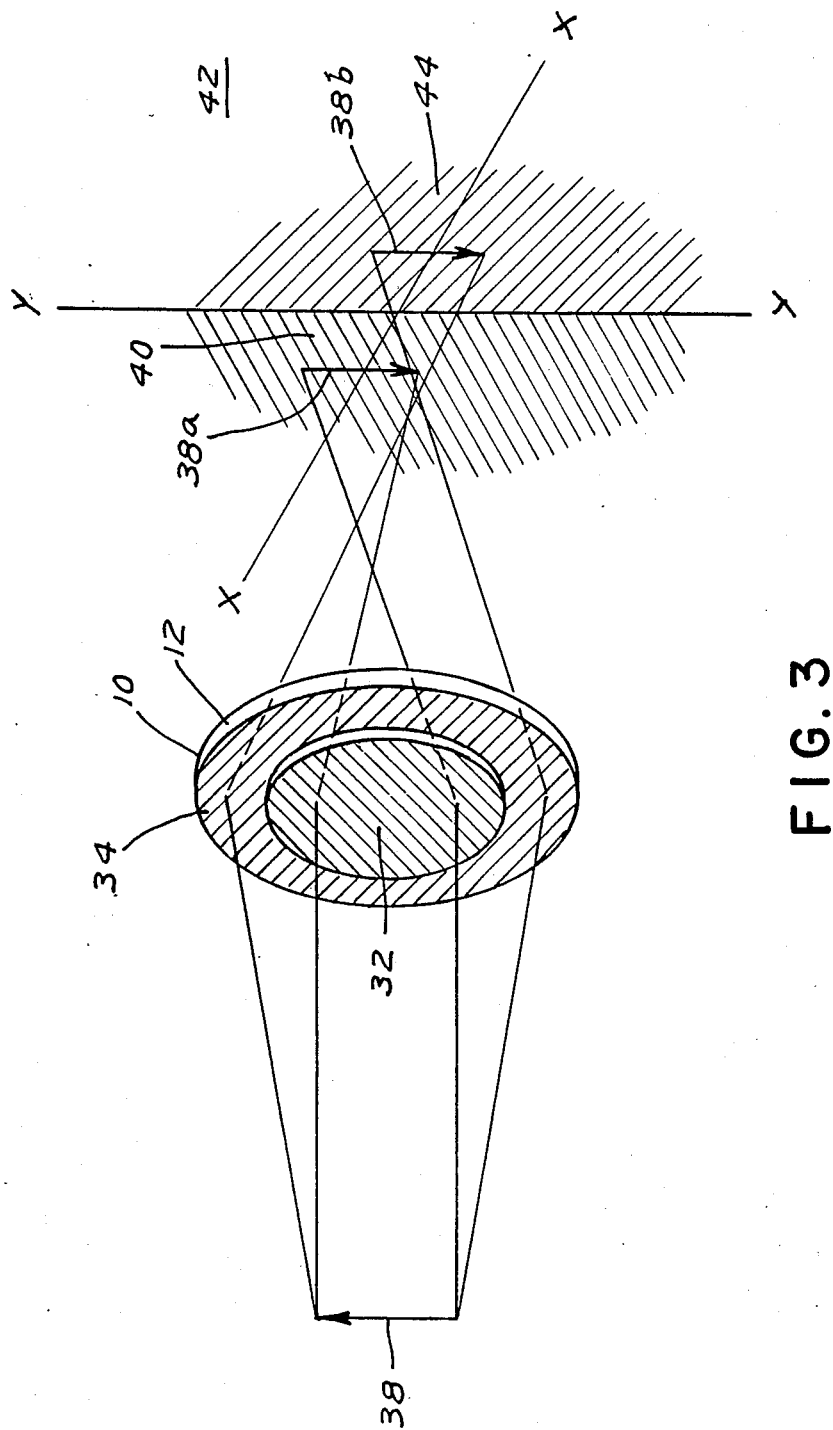
FIG. 3 illustrates a schematic view of an optical system according to this invention in which the laminated elements of the zone of focus hydrogel lens bring the incident rays to a focus on different areas of the retinal focal plane.

FIG. 3 illustrates a schematic view of an optic system according to this invention in which the laminated elements of the zone of focus hydrogel lens 10 bring the incident rays to focus on different areas of the retinal focal plane. Incidental rays of an object 38 traversing both the lens elements 32 and 34 will be brought to a focus in the form of an object 38 in the area 44 on the retinal focal plane 42. The amount of deflection given to the rays passing through the elements 32 and 34 will be the sum of the deflection provided by element 32 and that provided by element 34, while the deflection of rays incident only on element 34 will be angularly displaced only to the extent provided by that element.

Additionally, the incorporation of a prismatic correction to one or both of the lens elements 32 and 34 which produces images of objects on different portions of the retina, other than the image brought normally to a focus on the retinal focal area 42 by elements 32 and 34. For example, in addition to bringing incident rays to a focus on the retinal focal plane, lens element 32 can offer a prismatic correction to deflect refracted rays through lens element 34 to the left side of the retina. Similarly, a right directed prismatic correction of refracted rays in element 34 will cause the rays traversing lens element 34 to be brought to a focus on the retinal focal plane 42 on the right side of the retina.

The orientation of the prismatic correction may be placed to facilitate the accommodation of the brain to the dual images. While accommodation is enhanced by the physical displacement of the images to separate the distinct areas of the retina, it may be possible for an individual to adapt to images which are not physically isolated on the retina, but which are partially or totally superimposed. Accommodation may be enhanced in some individuals by developing each image in a different color. This can be done by adding a pigment to one or both of the lens elements 32 and 34 or by placing a colored membrane over either or both of the lens elements. While such an approach necessarily provides an unnatural colored aspect to the resulting image on the retina, this disadvantage may be outweighed by the increased ease of accommodation to the system. Further, the color can be added to only the lens element which is unique to the image of lesser importance to the individual, either the far or near object.

Figure 4A:
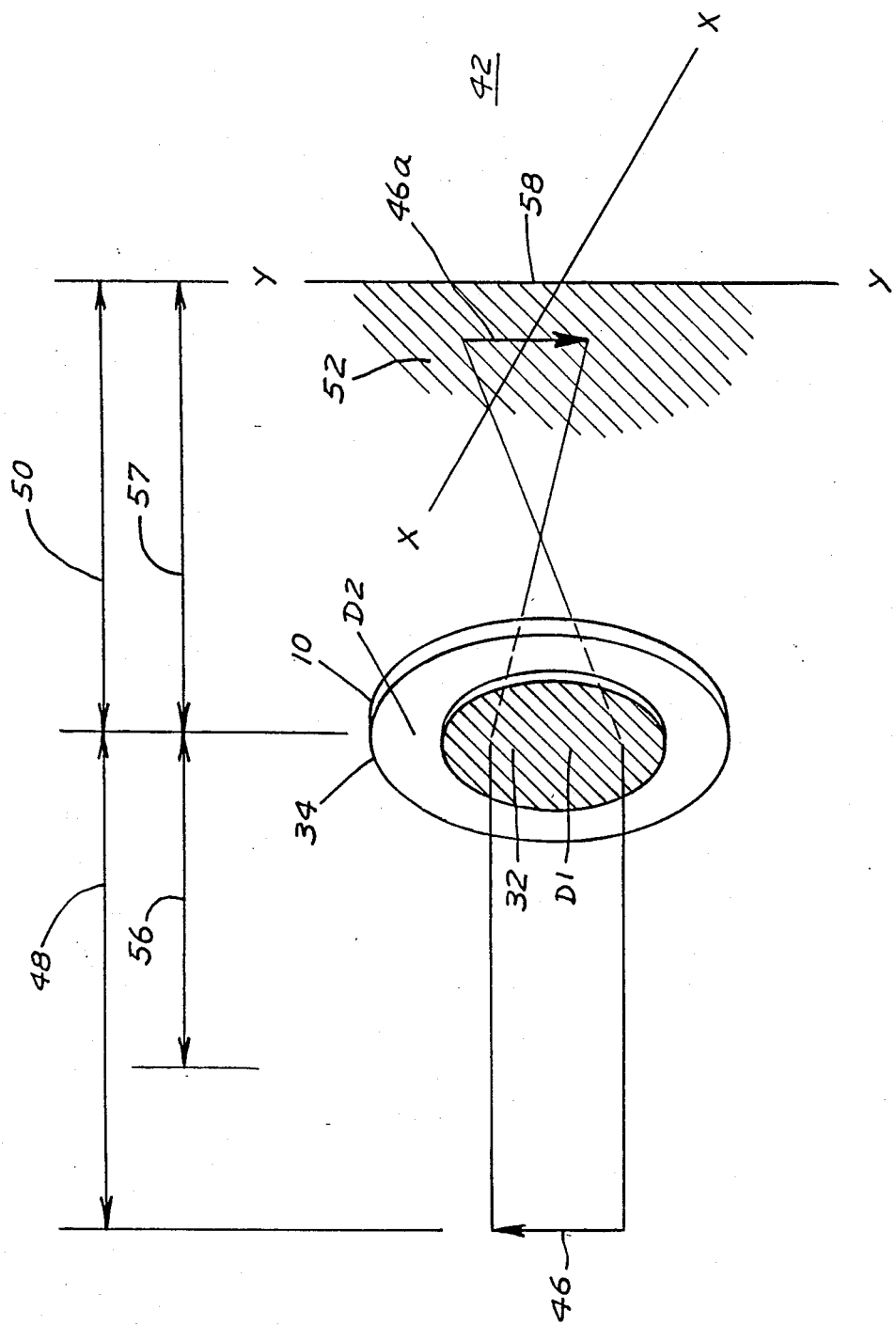
FIG. 4A and 4B illustrate schematic isometric views of an optical system in which the zone of focus hydrogel lens develops individual images for each area.
Figure 4B:
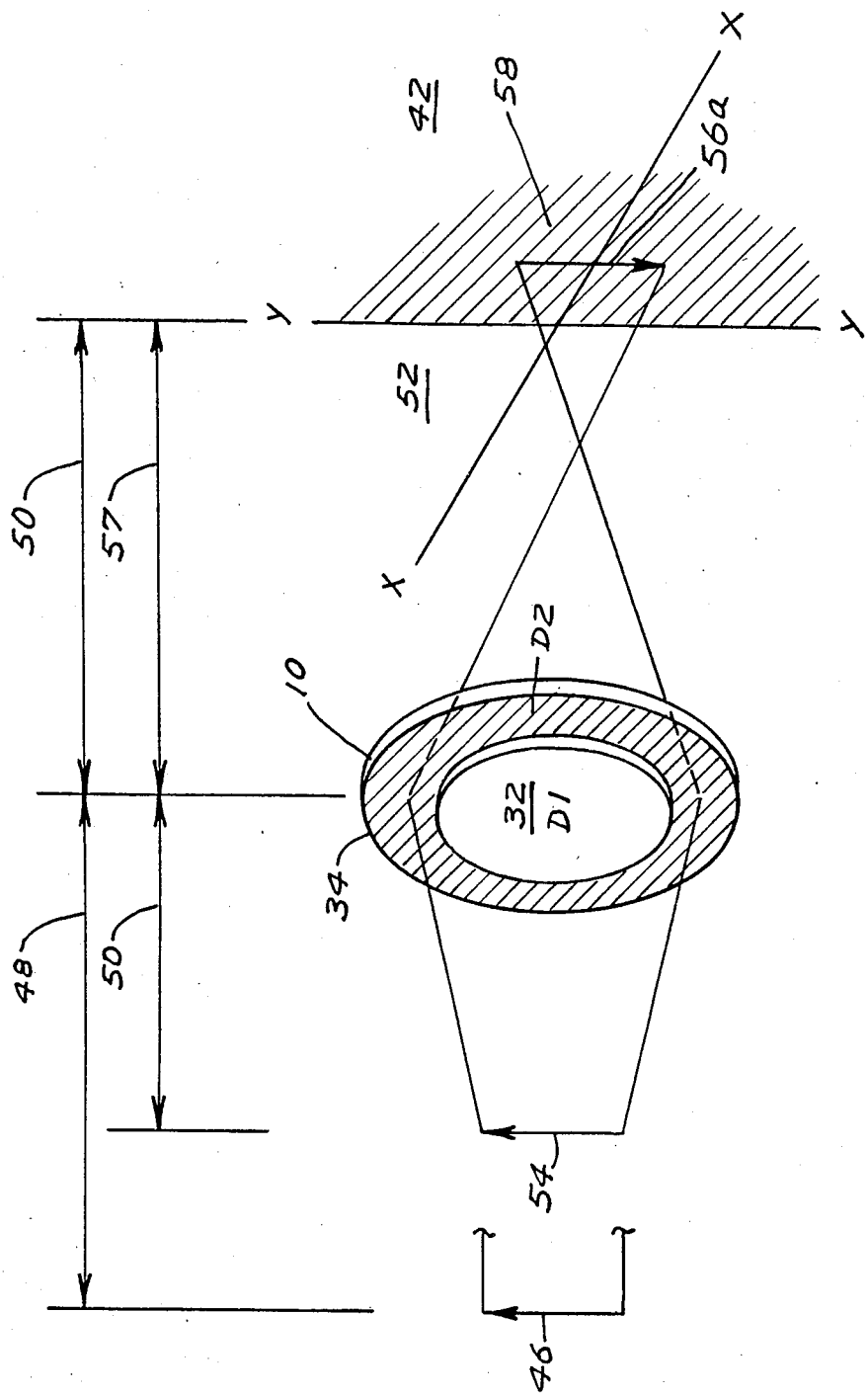

FIGS. 4A and 4B illustrate schematic views of an optical system utilizing the hydrogel lens of FIG. 1. In FIG. 4A the lens 10 has a plurality of hydrogel lens elements 32 and 34. Element 32 has a power D1 and element 34 has a power D2. The rays from far object 46 located at a far distance 48 are brought to a focus through lens elements 32 and 34 at a far focal distance 50 to produce an image 46a located in an area 52 of the retinal focal plane 42 indicated by an x-y axis.

In FIG. 4B the rays from a near object 54 at a near distance 56 passing through elements 32 and 34 are also brought to a focus at a near focal distance 57 to produce an image 56a in area 58 located in the retinal focal plane 42. Area 52 is generally the area to the left of the y axis and area 58 is generally the area to the right of the y axis. If the elements 32 and 34 have a left or right prismatic correction, the images 46a and 56a will be formed in different areas of the retina, illustrated generally by areas 52 and 58. The area 52 of FIG. 4A corresponds generally to the area 40 of FIG. 3 while the area 58 of FIG. 4B correspond generally to the area 44 of FIG. 3.

Figure 5:
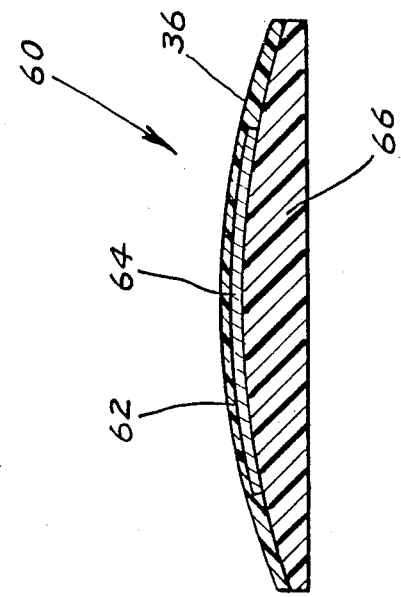
FIG. 5 illustrates a cross-sectional view of the laminated zone of focus hydrogel lens of the type shown in FIG. 1 taken along line 5—5 showing the colored portions of the lens.

FIG. 5 illustrates a hydrogel lens 60 including lens optic 62 in which at least one lens element of the lens 60 is colored. The lens element 64 is colored red so as to produce an image which is color distinguishable from the image produced by the element 66.

Figure 6:
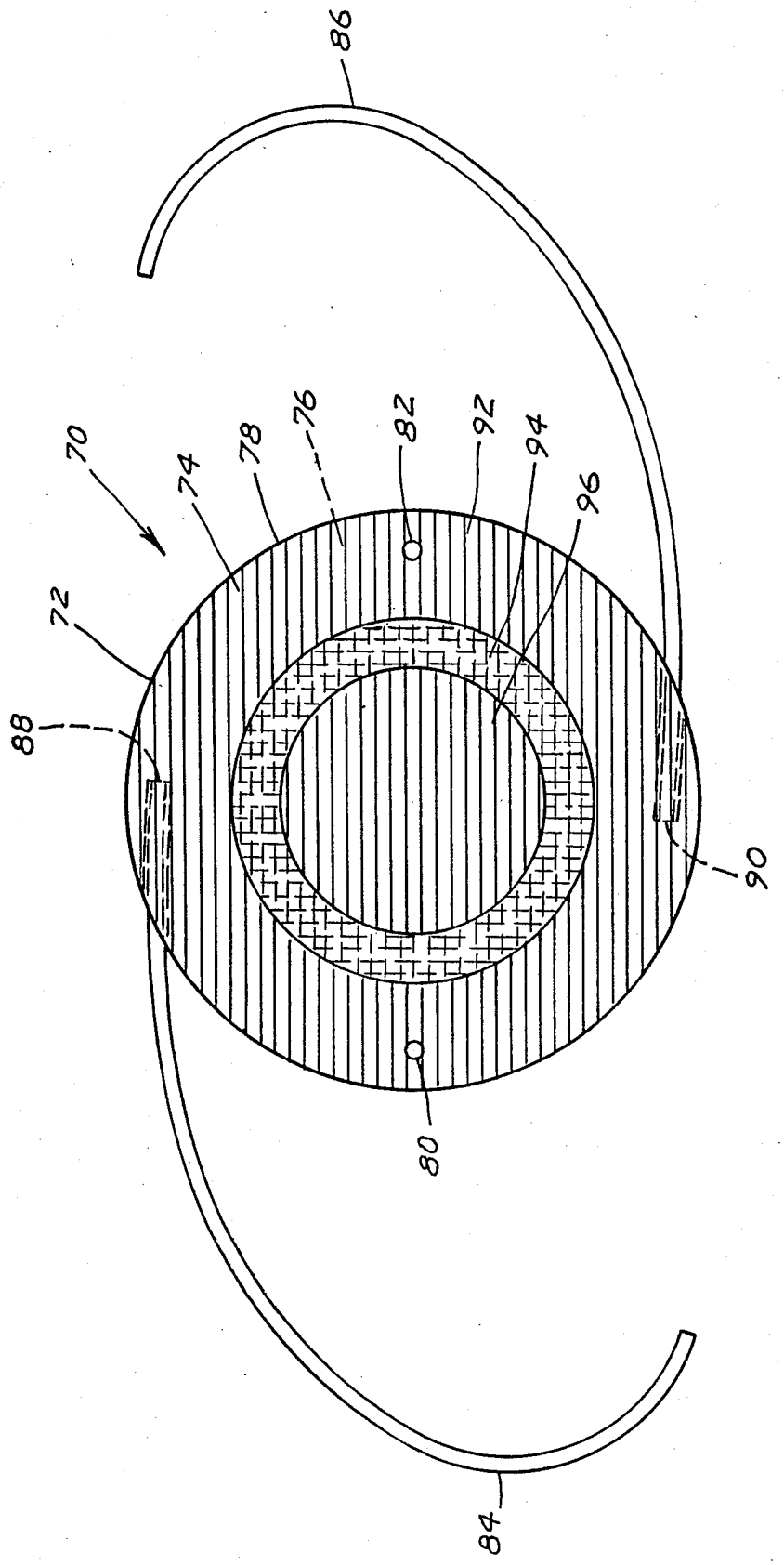
FIG. 6 illustrates a plan view of a laminated zone of focus hydrogel lens having three laminate elements; and, FIG. 7 illustrates a cross-sectional view of the lens element junction taken along line 7—7 of FIG. 1.

FIG. 6 illustrates a hydrogel lens 70 including an optic 72, a convex anterior surface 74, a plano posterior surface 76, an edge 78 therebetween, positioning holes 80 and 82, haptics 84 and 86 engaged in holes 88 and 90, and three laminated lens elements 92, 94 and 96. The lens elements may be clear or suitably colored with pigments in a fashion to produce images of three different colors to assist the patient in distinguishing between the images of the near, far and intermediate distance objects such as laminated lens elements 92 and 96 being blue and laminated lens element 94 being yellow. To this end, it must be recognized that the colored elements 92, 94, and 96 operate subtractively on the incident rays.

Figure 7:
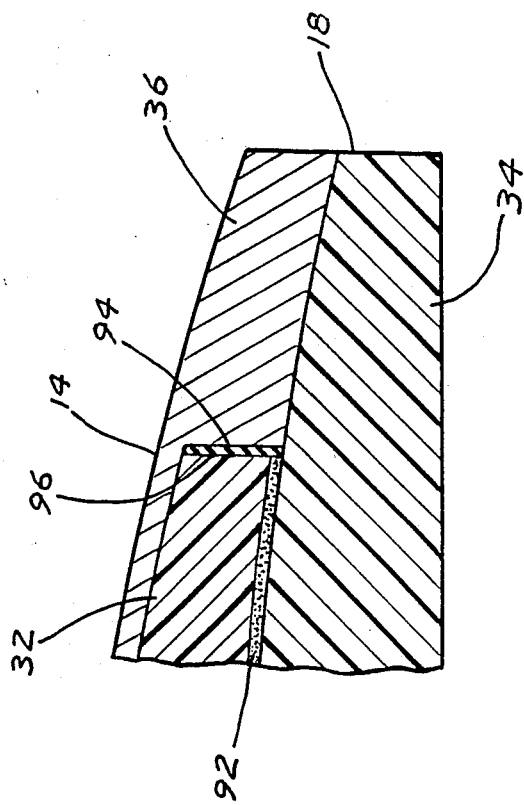

FIG. 7 illustrates a sectional view of the hydrogel lens 10 of FIG. 1 taken along line 7—7 of FIG. to illustrate the junction between the laminated elements. The smaller lens element 32 is joined to the larger lens element 34 by a layer of transparent adhesive 100. The adhesive material 100 may include an additive to provide anti-reflective characteristics. Alternatively, a conventional, discrete, anti-reflective highly pigmented opaque coating 102 may be applied to the periphery edge 104 of the smaller diameter lens element 32 to reduce extraneous light reflected from the edge 104 to mask rays which would otherwise produce reflections.

MODE OF OPERATION

In the case where a defective natural lens is to be replaced, it is customary to make extensive measurements on the eye prior to removal of the defective natural lens and to replace it with a fixed focus implantable lens. Such measurements allow the selection of a lens having appropriate power for the individual and also the nominal distance to the object which is desired to be brought in to focus on the retina. This approach to the problem has the disadvantage that a wide range of powers must be available to the surgeon. Since each lens is individually fabricated, the economic burden of fabricating a wide variety of powers adds substantially to the cost of the lenses. It would be much cheaper to manufacture only a few lenses and use them in all patients. The cost of manufacture would be reduced and inventory requirements would be less burdensome.

Reduction of the cost of the lenses would have the effect of increasing the availability of the procedure to those who currently lack the economic means to afford such an operation. This is the overriding consideration in medical care.

It is recognized that the technique of using less than the entire retina is usually not as desirable as a system which duplicates the normal lens use of the entire retina. There is a loss of acuity which shows up in reduced resolution and contrast, particularly in low light conditions. In addition, the accommodation of the brain to such a system takes a period of time and the degree of success varies with individuals.

The flexible hydrogel material allows the lens to be folded or rolled up and inserted into the eye through an incision or puncture which is much smaller than required for a conventional, rigid lens. Since the insertion procedure is simplified, the cost of implantation is reduced and the chance for success is enhanced.

Various modifications can be made to the present invention without departing from the apparent scope thereof.

I claim:

1. A laminated zone of focus hydrogel lens for use with an eye comprising:
    a. a first lamination hydrogel element encompassing a first area of said lens;
    b. a second lamination hydrogel element encompassing a second area of said lens;
    c. said first lamination element, in combination with said second lamination element serving to create an image of a first distinct portion of the retina; and,
    d. said second lamination element serving to simultaneously create an image on a second distinct portion of the retina which is, different from said first portion; wherein
    e. at least two of said laminated elements are of different colors.

2. A lens according to claim 1 where in said first and second lamination elements have differing indices of refraction.

3. A lens according to claim wherein said first lamination element has a surface curvature differing from the surface curvature of said second lamination element.

4. A lens according to claim wherein said first lamination element has a diameter less than said second lamination element.

5. A lens according to claim 4 wherein the surface area of said lens in the region of the periphery of the lamination element having the smaller diameter is coated with an opaque material to reduce reflected and refracted rays from this region.

6. A lens according to claim 1 wherein said lamination elements are joined with a transparent or non-transparent adhesive material.

7. A lens according to claim 1 further including a coating over at least one of the surfaces of said lens to provide a smooth surface.

8. A lens according to claim 7 wherein both surfaces of said lens are so coated.

* * * * *